US011225636B2

(12) United States Patent
Lundgren et al.

(10) Patent No.: US 11,225,636 B2
(45) Date of Patent: Jan. 18, 2022

(54) METHOD AND SYSTEM FOR CELL CULTIVATION

(71) Applicant: Cytiva Sweden AB, Uppsala (SE)

(72) Inventors: Bjorn Johan Lundgren, Uppsala (SE); Emmanuel Macedo, Uppsala (SE); Ann-Christin Magnusson, Uppsala (SE); Lena Maria Sandberg, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 45 days.

(21) Appl. No.: 15/573,960

(22) PCT Filed: May 16, 2016

(86) PCT No.: PCT/EP2016/060937
§ 371 (c)(1),
(2) Date: Nov. 14, 2017

(87) PCT Pub. No.: WO2016/188781
PCT Pub. Date: Dec. 1, 2016

(65) Prior Publication Data
US 2018/0291326 A1    Oct. 11, 2018

(30) Foreign Application Priority Data

May 28, 2015    (GB) .................................... 1509193

(51) Int. Cl.
*C12M 1/00*    (2006.01)
*C12M 1/12*    (2006.01)

(52) U.S. Cl.
CPC ............ *C12M 29/14* (2013.01); *C12M 25/16* (2013.01)

(58) Field of Classification Search
CPC ....... C12M 25/16; C12M 25/14; C12M 29/14
See application file for complete search history.

(56) References Cited

U.S. PATENT DOCUMENTS

| 5,043,431 | A | 8/1991 | Pungor, Jr. et al. | |
| 2005/0282269 | A1 | 12/2005 | Proulx | |
| 2006/0013061 | A1* | 1/2006 | Bivens | B01F 15/00194 366/16 |
| 2013/0081995 | A1 | 4/2013 | Larsen et al. | |
| 2014/0196791 | A1 | 7/2014 | Lee et al. | |

FOREIGN PATENT DOCUMENTS

| CN | 101298285 | A | | 11/2008 | |
| EP | 0046681 | A2 | | 3/1982 | |
| EP | 0674009 | A2 | | 3/1995 | |
| EP | 1020362 | A2 | * | 7/2000 | .......... B65B 55/025 |
| EP | 2623587 | A1 | | 8/2013 | |
| JP | H02-312583 | A | | 12/1990 | |
| JP | H06-269274 | A | | 9/1994 | |
| WO | WO-9833886 | A1 | * | 8/1998 | ............... C12N 7/00 |
| WO | 2009/139703 | A1 | | 11/2009 | |
| WO | 2011/139234 | A1 | | 11/2011 | |
| WO | 2014/110512 | A1 | | 7/2014 | |

OTHER PUBLICATIONS

Thermo Scientific Nunc Cell Factory Systems, pp. 1-4, downloaded from http://www.tslabor.hu/depo/NALGENE_Plastic/Nunc-Cell-Factory-Aseptic-Filling-Brochure-EN.pdf on May 31, 2019. (Year: 2014).*
Alfred et al. Efficient Suspension Bioreactor Expansion of Murine Enbryonic Stem Cells on Microcarriers in Serum-Free Medium; American Institute of Chemical Engineers, vol. 27, pp. 811-823. (Year: 2011).*
PCT International Search Report and Written Opinion for PCT Application No. PCT/EP2016/060937 dated Aug. 10, 2016 (8 pages).
GB Search Report for GB Application No. 1509193.7 dated Mar. 8, 2016 (4 pages).
Japanese Office Action for JP Application No. 2017-559606 dated Jan. 6, 2020 (6 pages with English translation).
Chinese Office Action for CN Application No. 201680030765.7 dated Sep. 30, 2020 (10 pages with English translation).

* cited by examiner

*Primary Examiner* — Sharmila G Landau
*Assistant Examiner* — Paul C Martin
(74) *Attorney, Agent, or Firm* — Eversheds Sutherland (US) LLP

(57) ABSTRACT

The present invention relates to a method and system for aseptic material transfer from a storage container to a bioreactor. More precisely the invention relates to a method and system for aseptically transferring dry material, such as microcarriers for cell cultivation, to a bioreactor, comprising transferring microcarriers from a first container housing said microcarriers to a bioreactor for cell cultivation via r transfer tubing connecting the first container to the bioreactor, wherein the transfer is accomplished with pressurized air or gas supplied to the container.

16 Claims, 3 Drawing Sheets

METHOD AND SYSTEM FOR CELL CULTIVATION

CROSS REFERENCE TO RELATED APPLICATIONS

This application claims the priority benefit of PCT/EP2016/060937 filed on May 16, 2016 which claims priority benefit of GB Application No. 1509193.7 filed May 28, 2015. The entire contents of which are hereby incorporated by reference herein.

FIELD OF THE INVENTION

The present invention relates to a method and system for aseptic material transfer from a storage container to a bioreactor. More precisely the invention relates to a method and system for aseptically transferring dry material, such as microcarriers, for cell cultivation to a bioreactor, comprising transferring dry material from a first container housing said material to a bioreactor for cell cultivation via transfer tubing connecting the first container to the bioreactor, wherein the transfer is accomplished with pressurized air or gas supplied to the container.

BACKGROUND OF THE INVENTION

Cell culture techniques have become vital to the study of animal cell structure, function and differentiation and for the production of many important biological materials, such as virus vaccines, enzymes, hormones, antibodies, interferon's, nucleic acids and virus vectors for gene therapy. Furthermore, cell culture and cell expansion is a very important step in cell therapy. For many cell culture approaches it is desired to expand a cell culture from a small to a large cell population.

For cell culture it is conventional to grow the cells on a cell adhering surface since most mammalian cells and certain other cells are anchorage-dependent to be able to grow. Conventional cell culture in tissue culture treated bottles or other vials give a limited yield of anchorage-dependent cells due to the small surface areas available.

Microcarrier culture introduces new possibilities and for the first time makes possible the practical high yield culture of anchorage-dependent cells. In microcarrier culture cells grow as monolayers on the surface of small spheres which are usually suspended in culture medium by gentle stirring. By using microcarriers in simple suspension culture systems it is possible to achieve yields of several million cells per milliliter and the systems are easily scalable.

In the microcarrier approach, cell culture is usually performed with beads in a spinner flask or beads packed in columns (perfusion culture). More recently, cell culture with microcarriers has been performed in disposable bioreactor, such as flexible bags. The microcarriers are for example dextran, cellulose or polyethylene based products.

In order to perform cell culture it is necessary to have sterile cell culture materials, such as drya culture media and microcarriers. The traditional way to sterilize microcarriers is via autoclaving outside of the bioreactor or inside the bioreactor via steam sterilization. With the introduction of single use bioreactors, it is no longer possible to perform the sterilization via steam in the bioreactor. Therefore it is necessary to provide pre-sterilized microcarriers which can be introduced into the bioreactor aseptically without compromising the sterility.

US2014/0196791 describes a single use bioreactor comprising a microcarrier container and a bioreactor vessel, wherein the microcarriers are transferred to the vessel by gravity or flushing with a fluid. Transfer with gravity will not be complete, i.e. some of the microcarriers will stick to the walls of the container and not be transferred to the bioreactor vessel. To improve this, flushing of the container is suggested with for example cell cultivation medium.

In spite of the many bioreactors known in the art there is still a need of improved methods and systems for aseptic transfer of dry materials, such as microcarrires, to bioreactors.

SUMMARY OF THE INVENTION

The present invention provides a method and system for aseptic transferal of dry materials, preferably microcarriers, to bioreactors. The system is useful with any type or size of bioreactor and is especially useful for large scale, single use bioreactors.

Thus, in a first aspect the invention relates to a method for aseptically transferring dry dry material for cell cultivation to a bioreactor, comprising transferring dry material from a first container housing said material to a bioreactor for cell cultivation via transfer tubing connecting the first container) to the bioreactor, wherein the transfer is accomplished with pressurized air or gas supplied to the container via a vent tubing including a dip tubing inserted into the container. The dip tubing prevents the whirling around of the dry material during introduction of the air or gas flow.

In one embodiment, the method comprises dosing of dry material from multiple containers by transferring a portion of dry material from a supply of dry material provided in a second container to the first container via transfer tubing between the containers. The transfer is performed with pressurized air or gas supplied to the second container via a vent tubing including a dip tubing inserted into the second container. Thereafter said portion of dry material which is now in the first container is transferred to the bioreactor with pressurized air or gas.

A number of portions but preferably at least two portions of dry material may be separately transferred from the second container to the first container and then each portion is separately transferred to the bioreactor. In this way it is not necessary to connect a new container to the bioreactor when more dry material is needed for the cell cultivation. This will minimize the risk of contamination of the cell culture further.

In a further embodiment, said portion of dry material transferred to the first container is weighed in the first container before being transferred to the bioreactor. This will guarantee that an exact amount of dry material is transferred to the bioreactor. Each portion may comprise for example, 1 g to 10's of kilos of dry materials giving a very flexible dosing range, depending on the size of the bioreactor and of the containers.

Preferably the container is turned upside down before transfer of the dry material with pressurized air or gas, wherein the dry material are at the bottom of the container and the dip tubing reaches above the level of the dry material.

The dry material may for example be microcarriers, dry media, such as dried or powdered cell culture media, or any other powders or salts.

In a second aspect, the invention relates to a transfer system comprising one or more rigid containers holding dry material; one or more flexible transfer tubings for transferring any dry material, such as microcarriers, from the container to a bioreactor or to a first container from a second container; one or more flexible vent tubings including a dip tubing inserted in the container and connected to a source of pressurized air or gas. Preferably the tubings are provided with valves and connectors to connect the tubings to the bioreactor and/or further containers. Preferably the vent tubing is provided with a sterile vent filter. Alternatively, sterile gas or air is used. Preferably the containers are bottle shaped and provided with an upper ported cap in which the tubings are attached to the containers. The containers or bottles and their contents of dry material may have any suitable size depending on the bioreactor size and the needs of the cell cultivation. Examples of container sizes are from 100 mL to 5 L and examples of bioreactor sizes are from 1 L to 10000 L. When more than one container is used in the transfer system, they may be of the same or different size.

Preferably the transfer system is sterilized by any type of sterilization, most preferably by gamma radiation.

In one embodiment the container, which is connected to the bioreactor, may be placed on a scale for weighing the amount of dry material transferred to the bioreactors which will be described more closely in the detailed section below.

In a third aspect the invention relates to use of the above transfer system in a cell culture process, wherein microcarriers are provided to the bioreactor at any desired time in the process. The microcarriers are provided at the beginning of the process and at any time and in any number thereafter before the end of the process. In one embodiment the transfer system is preferably connected to the bioreactor during the whole process, especially when there is a need of adding more microcarriers during the process.

DETAILED DESCRIPTION OF THE INVENTION

The transfer system of the invention and its method of use will now be described more closely in association with the accompanying drawings. Although the method and transfer system is suitable for transferring any type of dry material the detailed description below is described in connection with microcarriers for cell cultivation as the dry material.

The present invention relates to a method and transfer systems for aseptic transfer of dry material, such as microcarriers, to bioreactors. The transfer system is a separate unit from the bioreactor and can be used with any type of bioreactor in any scale. Microcarriers used in the invention are kept sterile in specially designed containers enabling direct transfer of microcarrier beads into a bioreactor in an aseptic manner. This will considerably improve the current procedure as it avoids the tedious and time consuming preparative sterilization practiced in the pharmaceutical industry, in which microcarrier beads are swollen, washed with buffer and autoclaved before being added to the cell culture vessel (bioreactor), and then washed with cell culture media.

Figure 1:
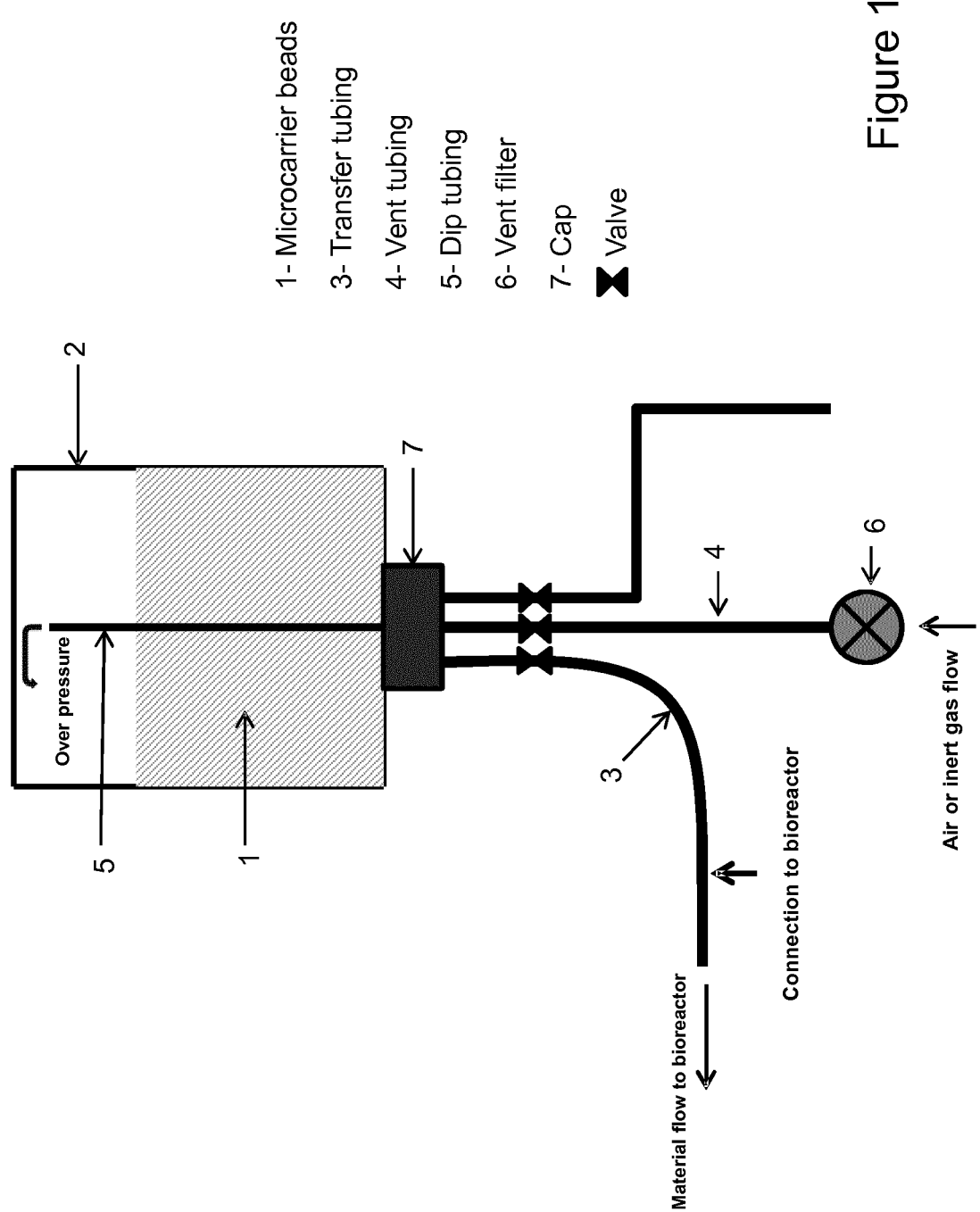
FIG. 1 is a schematic view of the transfer system of the invention in a position ready to use, i.e. the container has been turned upside down for transfer of dry material from a first container into a bioreactor.

With reference to FIG. 1, the transfer system comprises dry microcarriers 1 housed in a container 2 which preferably is shaped like a bottle having a ported cap 7 through which transfer tubing 3 and vent tubing 4 is connected to the container 2. In FIG. 1 the container or bottle 2 is shown in an upside sown position wherein the microcarriers 1 will be located at the bottom of the container closest to the cap 7 and the dip tube 5 will reach above the level of the microcarriers to enable inflow of pressurized air or gas into this space of the container which effectively will transfer the microcarriers through the transfer lines 3 to a bioreactor (not shown) or from a further container 2A to the container 2 as shown in FIG. 2.

Figure 2:
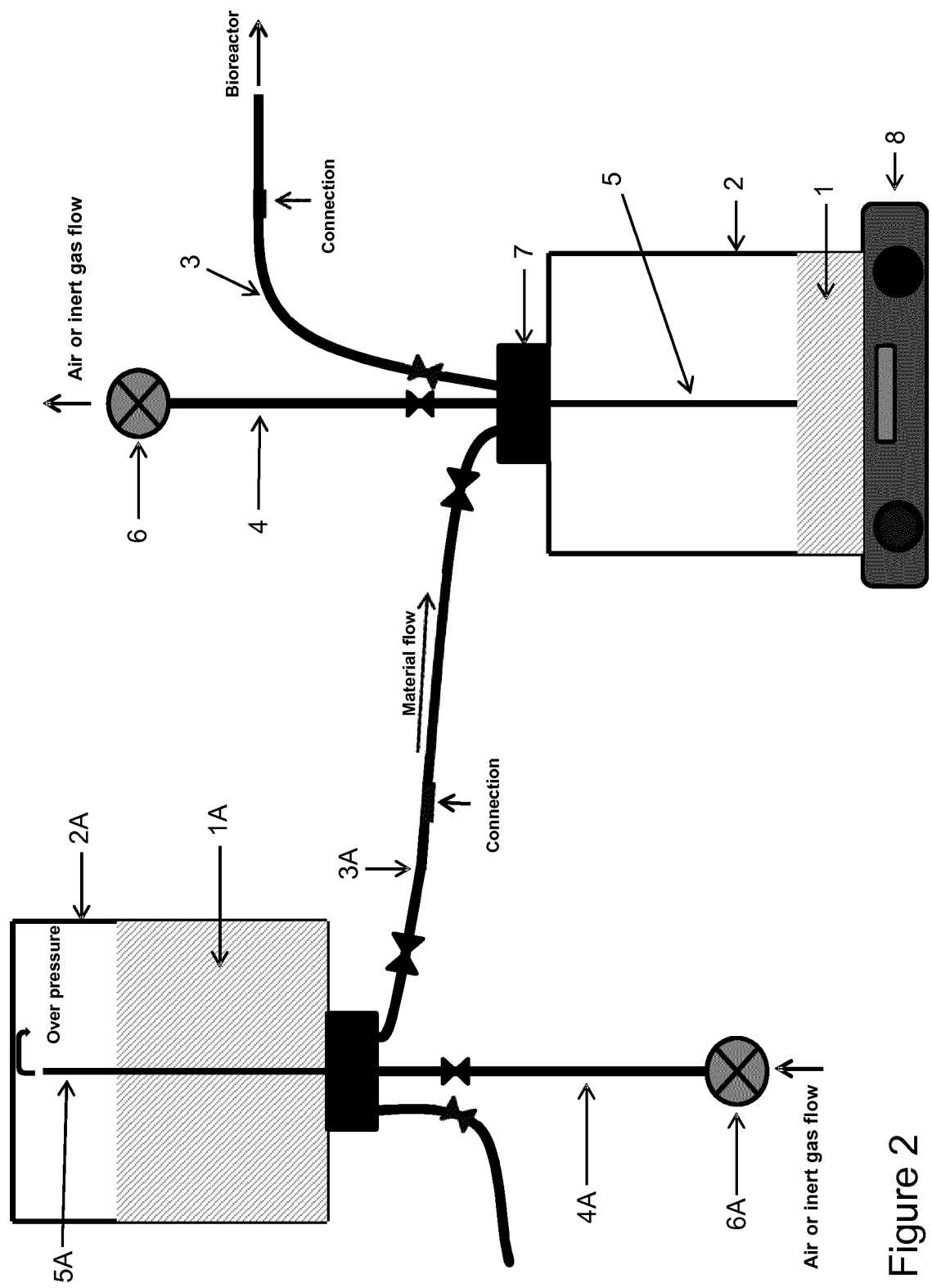
FIG. 2 is a schematic view of the transfer system of the invention in a position for transferring a portion of the total amount of dry material from a first container to a second container wherein the second container is placed on a scale and the transfer is continued until a desired weight of the dry material is obtained in the second container.

FIG. 2 shows a preferred embodiment in which dry microcarriers 1A are transferred from a second container 2A, which is positioned upside-down, to the first container 2 by connecting a source of pressurized air or gas to a vent filter 6A. In this embodiment not all microcarriers from the second container 2A are transferred to the container 2 at the same time. On the contrary, separate portions or doses of the microcarriers 1A are transferred to the bioreactor via container 2 according to the needs of the cell culture procedure. To ensure that a correct amount of microcarriers are transferred from container 2A to container 2 and then to the bioreactor, the container 2 is place on a scale 8. This avoids the needs of connecting a new container 2 to the bioreactor every time there is a need of new additions of microcarriers to the cell culture in the bioreactor.

The microcarriers 1, 1A used in the invention are preferably Cytodex™ (GE Healthcare Bio-Sciences AB) microcarriers but any type of microcarriers may be used.

Figure 3:
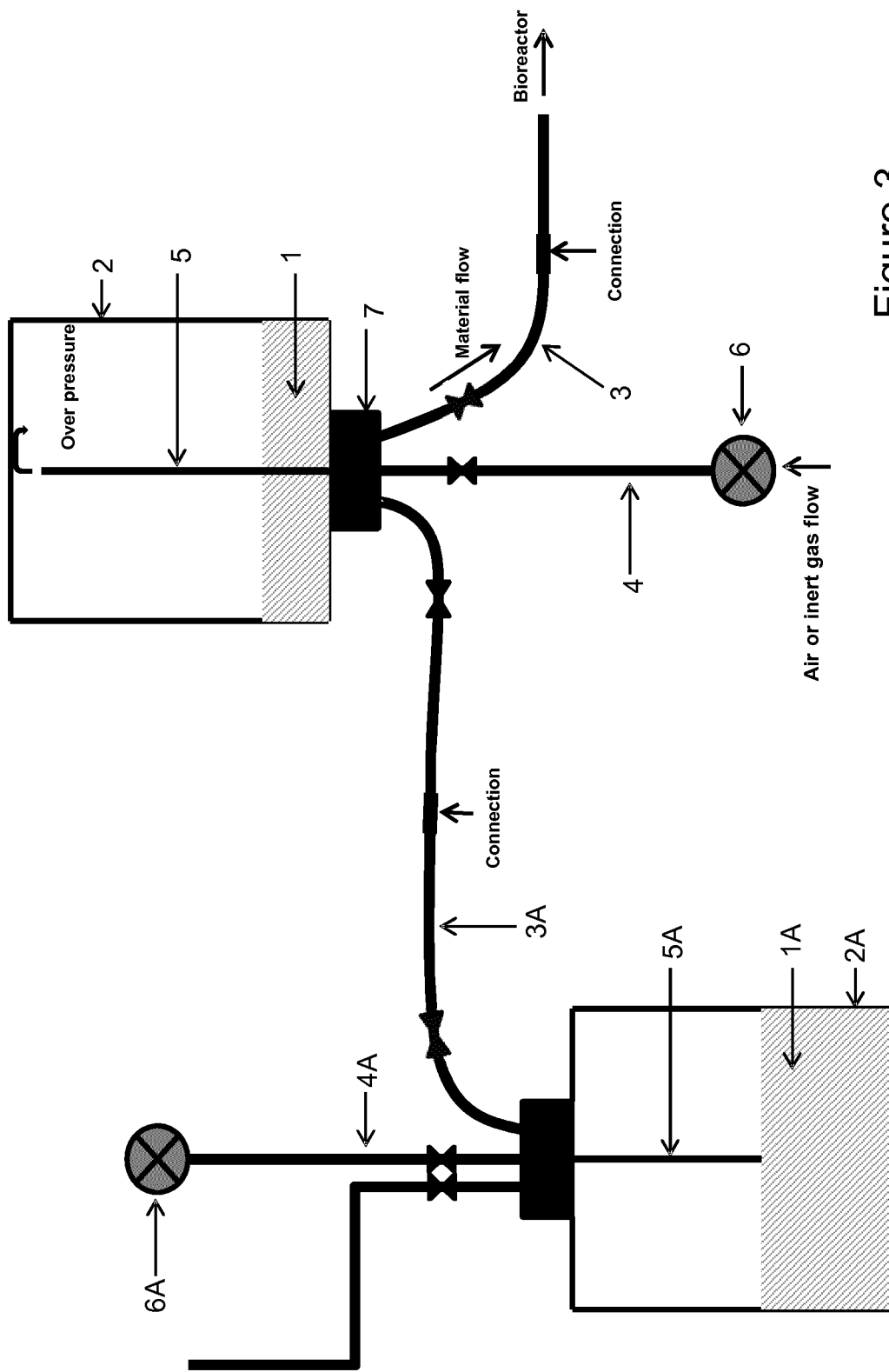
FIG. 3 shows a position of the transfer system in which the second container of FIG. 2 has been turned upside down and the transfer system is ready for use to transfer dry material from the second container to the bioreactor via pressurized air or gas.

FIG. 3 shows the positioning of containers 2, 2A following completed transfer of a desired portion of microcarriers from container 2A to container 2. In this position the container 2A has been brought back into its upright position and instead container 2 is turned upside down. When pressurized air or gas is supplied to the container 2 the weighed microcarriers in container 2 will be transferred from container 2 to the bioreactor (not shown). This procedure, i.e. the filling of microcarriers from container 2A to container 2 according to FIG. 2, and then the transfer to the bioreactor according to FIG. 3, may be repeated an optional number of times.

In the method of the invention the sterile containers 2, 2A are readily connected to the bioreactors via tubing using an aseptic connector or a welding connection, to provide a connection for transfer of the microcarrier beads into the bioreactor. Transfer will be achieved by using a slight over pressure of sterile air or nitrogen introduced in the container via a dedicated port, after turning the container upside down.

All the materials used for the transfer system, directly in contact with sterile microcarrier beads, will meet USP class VI requirements (biological test for plastics). The transfer system of the invention including microcarrier beads preferably withstands a maximum gamma irradiation dose of at least 40 KGy.

The microcarriers used in the invention preferably are provided in rigid plastic container, such as PET containers. Each container is preferably equipped with a suitable 3-ported cap 7 and two transfer ports fitted with a tubing 3, 3A of suitable length, such as a TPE (thermoplastic elastomer) tubing. In one embodiment one transfer tube may be equipped at its remaining end with a ReadyMate™ aseptic connector (for ReadyMate aseptic connection) whereas the second one will be double sealed for subsequent welding connection. In another embodiment both transfer lines are double sealed. The third port will be equipped with a vent tubing 4, 4A, such as a silicon vent tubing, fitted with a vent filter, such as a 0.2 µm vent filter, for introduction of slightly compressed air or nitrogen (max. 0.5 bar) for the transfer of microcarriers into the bioreactor.

The two transfer ports 3, 3A will allow simultaneous multiple aseptic connections, or subsequent aseptic connections, by for example welding, to other bioreactors should a container not be completely emptied after a previous run. The 3-ported cap is also equipped with an internal spigot which is directly connected to the external vent port. This spigot will be fitted with a polymeric dip tube to bring the slightly compressed air or nitrogen over the level of the microcarrires (once the container is turned upside down) and press thereby material out of the container without any major turbulence (FIG. 2-3).

The container system of the invention can be easily connected to bioreactors via any connection, such as a ReadyMate or by only welding aseptic connection. After turning the container upside down, connection is opened and microcarriers are transferred by introducing a slight overpressure of air or inert gas (FIG. 2).

If required, aseptic connection can also be achieved by welding, providing that the container and the bioreactor are having the same kind of tubing with matching diameters.

Should the contents of microcarriers in one container not be enough, then it will be possible to transfer in an aseptic manner extra material to the bioreactor following the procedure described below, see FIG. 2-3:

Place the emptied first container 2 on a balance.

Connect, for example by welding, a tubing 3A on a second container 2A filled with a supply of microcarriers to the remaining tubing 3 available on the emptied container 2 (FIG. 2).

Turn the second container 2A upside down and transfer/weigh the desired amount of microcarriers from the container 2A to the container 2 using a slight over pressure of air or nitrogen introduced via the sterile vent tubing on the new container or pack.

Once the required amount of material has been weighed, connection between the new container 2A and the bioreactor-connected container 2 is closed, and the latter is turned upside down. The newly weighed material is then transferred into the bioreactor using a slight over pressure of air or inert gas introduced via vent tubing on the container directly connected to the bioreactor (FIG. 3).

If welding is the selected method to connect the microcarrier container to a bioreactor, then the bioreactor should be provided with the same kind of tubing of the same diameter as the microcarrier container. If connection between the microcarrier container and bioreactor is to be achieved via ReadyMate™ aseptic connector, then there should be a ReadyMate™ connector available on bioreactor tubing.

Both transfer and vent tubing are equipped with valves, such as pinch valves, allowing selective opening/closure under transfer operations. The valves are preferably made of a material withstanding gamma irradiation.

The container system of the invention will be filled with microcarriers, preferably Cytodex™ microcarriers, in an environment with controlled bioburden. After filling and closing with the ported caps, the container system will be enclosed/sealed in a double plastic film protection (secondary/tertiary packaging) and packed in a cardboard box. The card board box with its contents is then gamma sterilized and the shelf life will be at least 2 years at 30° C.

The invention claimed is:

1. A method for aseptically transferring dry material for cell cultivation to a bioreactor from a first container and a second container, comprising:
    introducing pressurized air or gas into the second container via a first dip tube inserted into the second container to cause the dry material from the second container be transferred via a first transfer tubing between the containers to the first container until a predetermined weight of the dry material is obtained in the first container, wherein the second container is turned upside down during the transfer of the dry material to the first container with pressurized air or gas, wherein the dry material is at the bottom of the inverted second container and the end of the first dip tube is above the level of the dry material;
    weighing a portion of the dry material transferred to the first container in the first container;
    introducing pressurized air or gas via a second dip tube inserted into the first container to cause the dry material from the first container to be transferred to the bioreactor for cell cultivation via a second transfer tubing connecting the first container to the bioreactor; and
    closing the connection between the second container and the first container,
    wherein the first container is turned upside down before transfer of the dry material to the bioreactor with pressurized air or gas, and wherein the dry material is at the bottom of the inverted first container and the end of the second dip tube is above the level of the dry material.

2. Method according to claim 1, wherein at least two portions of dry material are separately transferred from the dry material in the second container to the first container and then each portion is separately transferred to the bioreactor.

3. Method according to claim 1, wherein the dry material is selected from microcarriers, dried media, powder or salts.

4. Method according to claim 3, wherein the dry material is microcarriers for cell cultivation.

5. Method according to claim 1, wherein the bioreactor is single use.

6. Method according to claim 1, wherein at least one of the first container or the second container is rigid.

7. Method according to claim 6, wherein the first and second containers are bottle shaped.

8. Method according to claim 1, wherein the first and second transfer tubing comprise valves.

9. Method according to claim 1, wherein the first and second containers can hold 100 mL to 5 L.

10. Method according to claim 1, further comprising disconnecting the bioreactor from the first container after the dry material has been transferred from the first container into the bioreactor.

11. A method for aseptically transferring two or more portions of a dry material for cell cultivation to a bioreactor from a first container and a second container, comprising the following steps:
    1) introducing pressurized air or gas into the second container via a first dip tube inserted into the second container to cause a first portion of the dry material from the second container be transferred via a first transfer tubing between the containers to the first container until a predetermined weight of the dry material is obtained in the first container, wherein the second container is turned upside down during the transfer of the first portion of the dry material to the first container with pressurized air or gas, wherein the dry material is at the bottom of the inverted second container and the end of the first dip tube is above the level of the dry material;
2) weighing the first portion of the dry material transferred to the first container in the first container;
3) introducing pressurized air or gas via a second dip tube inserted into the first container to cause the first portion of the dry material from the first container to be transferred to the bioreactor for cell cultivation via a second transfer tubing connecting the first container to the bioreactor;
4) closing the connection between the second container and the first container, wherein the first container is turned upside down before transfer of the dry material to the bioreactor with pressurized air or gas, and wherein the dry material is at the bottom of the inverted first container and the end of the second dip tube is above the level of the dry material;

5) opening the connection between the second container and the first container; and 6) repeating steps 1-5 one or more times.

12. Method according to claim 11, wherein the dry material is selected from microcarriers, dried media, powder or salts.

13. Method according to claim 11, wherein each portion comprises 1 gram to 10 kilograms of dry material.

14. Method according to claim 11, wherein prior to step 1, the first container, second container, first dip tube, second dip tube, first transfer tubing, and second transfer tubing are sterilized by gamma radiation.

15. Method according to claim 11, wherein the dry material is microcarriers for cell cultivation.

16. Method according to claim 11, wherein the pressurized air or gas comprises nitrogen gas.

* * * * *